United States Patent [19]

Li et al.

[11] Patent Number: 5,589,046
[45] Date of Patent: Dec. 31, 1996

[54] ROOM TEMPERATURE CARBON MONOXIDE GAS SENSOR AND THE PROCESS FOR PREPARING THE SAME

[75] Inventors: Wenfan Li; Xiuying Liu, both of Changchun, China

[73] Assignee: Chang Chun Institute of Applied Chemistry of the Chinese Academy of Sciences, Changchun, China

[21] Appl. No.: 358,217

[22] Filed: Dec. 16, 1994

[30] Foreign Application Priority Data

Mar. 17, 1994 [CN] China ................ 94101843.1

[51] Int. Cl.⁶ .................... G01N 27/12; G01N 27/26
[52] U.S. Cl. .................... 204/424; 204/421; 264/56; 264/60; 264/104; 422/98; 427/58; 427/126.3; 427/374.1
[58] Field of Search ................ 204/153.1, 153.18, 204/421, 400, 424–429; 422/98; 264/56, 60, 104; 427/58, 126.3, 374.1

[56] References Cited

U.S. PATENT DOCUMENTS

| | | |
|---|---|---|
| 3,865,550 | 2/1975 | Bott et al. .................... 422/98 |
| 4,111,658 | 9/1978 | Firth et al. .................... 422/98 |
| 4,242,302 | 12/1980 | Kitamura et al. .................... 422/98 |
| 5,226,309 | 7/1993 | Stetter et al. .................... 422/98 |
| 5,228,975 | 7/1993 | Yamada et al. .................... 204/421 |

FOREIGN PATENT DOCUMENTS

| | | |
|---|---|---|
| 89102921.4 | 6/1989 | China . |
| 92110578.9 | 6/1992 | China . |

*Primary Examiner*—T. Tung
*Attorney, Agent, or Firm*—Pennie & Edmonds

[57] ABSTRACT

The present invention relates to a room temperature carbon monoxide gas sensor and a process for preparing the same. The said sensor is prepared by using $SnO_2$ as base material, $Y_2O_3$, $La_2O_3$, Cr, Pt black and $Al_2O_3$ as additives, after grinding, sintering and aging steps, a sensor which can quantitative and selectively detect carbon monoxide in the atmosphere having a carbon monoxide concentration in the range of 25–600 ppm is obtained. Due to the addition of high purity Cr, the rate of adsorb and desorption of gases of the sensor of the present invention is accelerated, the response and recovery time are less than 10 and 15 seconds respectively.

2 Claims, No Drawings

ROOM TEMPERATURE CARBON MONOXIDE GAS SENSOR AND THE PROCESS FOR PREPARING THE SAME

FIELD OF THE INVENTION

The present invention relates to a semiconductor sensor used for detecting carbon monoxide gas at room temperature and the process for preparing the same.

BACKGROUND OF THE INVENTION

In order to avoid of carbon monoxide gas poisoning, to control the burning process, or to provide the pre-alarm of a fire disaster, semiconductor gas sensor detecting carbon monoxide gas at its low concentration by the utilization of the electric conductance changes of a metal oxide semiconductor in carbon monoxide atmosphere, are used. At present, all of the semiconductor gas sensors for detecting carbon monoxide gas are heater sensors. The TGS 203 type gas sensor manufactured by Figaro Engineering Inc. of Japan is operated in the mode of high and low temperature heating cycles; it detects the carbon monoxide gas at 80° C. and the gas molecules are then desorbed at 300° C. The major raw material of this kind of sensor is $SnO_2$, with additives of 0.4% by weight of Pd and 50% by weight of $X-Al_2O_3$. (N. Murakami, K. Takahata and T. Seiyama, Proc. 4th Int. Conf. Solid-state Sensors and Actuators, Tokyo, Japan, CN92110578.9 (Changchun Institute of Applied Chemistry, Chinese Academy of Sciences) discloses "A process for preparing a room temperature carbon monoxide gas sensor". According to the process of CN92110578.9 $SnO_x$ is used as the base material, while $Al_2O_3$, MgO, Pt, Pd and $ThO_2$ are used as additives for preparing the said gas sensor, wherein, the value of x is in the range of 1.0–1.6. The carbon monoxide gas sensor prepared according to this process can detect carbon monoxide at room temperature; the surface temperature of the sensor is low, the energy consumption of the sensor is low; the application circuit is simple. However, this gas sensor has the following disadvantages: long oscillation cycle period (50–100 seconds), and short service life. In addition, since $ThO_2$ is used, the sensor obtained by the said process has some radio-activity.

CN89102921.4 (Changchun Institute of Applied Chemistry, Chinese Academy of Sciences) discloses "A room temperature semiconductor gas sensor". The said semiconductor gas sensor is mainly used for detecting coal gas and liquefied petroleum gas. The ratio of the raw materials used in this sensor is as follows: $SnCl_4/SnO_2$ is in the range of 0.5–1.5 (weight); oxides of rare earth metals $SnO_2$ is in the range of 0.5–1(weight), wherein, the said oxides of rare earth metals are only $LaO_2$ and $CeO_2$. Similarly, the said gas sensor has the disadvantages of long oscillation cycle period (50–100 seconds) and short service life(less than 45 days).

OBJECT OF THE INVENTION

One object of the present invention is to provide a room temperature carbon monoxide gas sensor which can be prepared and used safely, and has short oscillation cycle period and long service life (over 1 year).

Another object of the present invention is to provide a process for preparing the above-mentioned room temperature carbon monoxide gas sensor.

SUMMARY OF THE INVENTION

The present invention provides a room temperature carbon monoxide gas sensor comprising two helical coil electrodes made from a Pt filament of a diameter of 0.03–0.05 mm. One of the helical coils has a greater diameter than the other one. Preferably, the length of the helical coils is in the range of 0.8–1.4 mm. Preferably, the one having a greater diameter has a diameter in the range of 0.6–1 mm and it is used as an anode. While the other one has a diameter between 0.3–0.6 mm and it is used as a cathode. The smaller diameter coil is inserted into the greater diameter coil. The two helical coil electrodes are prepared by coating the Pt filament with a composition containing $SnO_2$ as base material, and $Y_2O_2$, $La_2O_3$, Cr, Pt black and $Al_2O_3$ as additives.

The present invention also provides a process for preparing the above-mentioned room temperature carbon monoxide gas sensor, which comprises the following steps:

(1) preparing two helical coil electrodes with a Pt filament of a diameter of 0.03–0.05 mm. One of the coils has a greater coil diameter; the other one has a smaller coil diameter The length of the coils is in the range of 0.8–1.4 mm. The greater diameter coil has a diameter in the range of 0.6–1 mm and it is used as an anode, while the other coil has a diameter between 0.3 –0.6 mm and it is used as a cathode;

(2) adding $SnO_2$, $Y_2O_3$, $La_2O_3$, Cr, Pt black and $Al_2O_3$ into an agate mortar at a certain proportion, and then adding de-ionized water into the agate mortar to grind the mixture into a paste-like mixture;

(3) coating the paste-like mixture obtained in step (2) onto the surface of the electrodes obtained in step (1), and then inserting the smaller electrode into the bigger electrode to prepare a globular sensor;

(4) drying the globular sensor obtained in step (3), and then sintering the dried globular sensor at a temperature in the range of 780°–900° C. in air for about 80–130 minutes, before cooling and aging the sensor for about 168 hours, thus obtaining a room temperature carbon monoxide gas sensor.

DETAILED DESCRIPTION OF THE INVENTION

The present invention provides a room temperature carbon monoxide gas sensor comprising two helical coil electrodes made from a 0.03–0.05 mm Pt filament, one of which having a greater coil diameter, and the other one having a smaller coil diameter, the length of the coils being in the range of 0.8–1.4 mm, the bigger one having a diameter in the range of 0.6–1 mm and being used as an anode, while the smaller one having a diameter between 0.3–0.6 mm and being used as a cathode, the smaller electrode being inserted within the bigger one, wherein, the two electrodes are coated by a composition having the following composition:

1 part (weight) of high purity SnO2;

0.002–0.08 part (weight) of high purity Pt black;

0.00025–0.065 part (weight) of high purity $Y_2O_3$;

0.00009–0.086 part (weight) of high purity $La_2O_3$;

0.00015–0.08 part (weight) of high purity Cr; and 0.0002–0.07 part (weight) of high purity $Al_2O_3$.

According to the present invention, the term "high purity" means that the purity of the materials used is higher than 99.99%.

The present invention also provides a process for preparing the above-mentioned room temperature carbon monoxide gas sensor, which comprises the following steps:

(1) preparing two helical coil electrodes with 0.03–0.05 mm Pt filament, one of which having a greater coil diameter, and the other one having a smaller coil diameter, the length of the coils being in the range of 0.8–1.4 mm, the bigger one having a diameter in the range of 0.6–1 mm and being used as an anode, while the smaller one having a diameter between 0.3–0.6 mm and being used as cathode a;

(2) adding $SnO_2$, $Y_2O_3$, $La_2O_3$, Cr, Pt black and $Al_2O_3$ into an agate mortar at the following proportion,
1 part (weight) of high purity $SnO_2$;
0.002–0.08 part (weight) of high purity Pt black;
0.00025–0.065 part (weight) of high purity $Y_2O_3$;
0.00009–0.086 part (weight) of high purity $La_2O_3$;
0.00015–0.08 part (weight) of high purity Cr; and
0.0002–0.07 part (weight) of high purity $Al_2O_3$,
and then adding de-ionized water into the agate mortar to grind the mixture into a paste-like mixture;

(3) coating the paste-like mixture obtained in step (2) onto the surface of the electrodes obtained in step (1), and then inserting the smaller coil electrode into the bigger coil electrode to prepare a sensor having spiral shape;

(4) drying the spiral shape sensor obtained in step (3), and then sintering the dried globular sensor at 780°–900° C. in air for about 80–130 minutes, before cooling and aging it for about 168 hours, thus obtaining a room temperature carbon monoxide gas sensor.

The sensor of the present invention can quantitatively and selectively detect carbon monoxide at room temperature. When the sensor of the present invention is used, the strength of signals produced by any one of the interfering gases selected from the group consisting of 500 ppm methane gas, 500 ppm propane gas, 400 ppm butane gas, 200 ppm ethanol gas and 400 ppm ethyl acetate gas is smaller than that produced by 60 ppm carbon monoxide, and these interfering gases have no interference on detecting carbon monoxide in an atmosphere having a carbon monoxide concentration of 100 ppm. When the concentration of carbon monoxide is in the range of about 25–600 ppm, the sensitivity of the sensor of the present invention can be calculated by the following equation:

$$\Delta I = I_{max} - I_{min},$$

wherein, $I_{max}$ is the maximum current of the sensor in the gas being detected, while $I_{min}$ is the minimum current of the sensor in the gas being detected.

Owing to the addition of high purity Cr, the rate of absorption and desorption of gases of the sensor of the present invention is accelerated, the response and recovery time is shorten. In fact, the response time is less than 10 seconds, and the recovery time is less than 15 seconds. In addition, the oscillation cycle period is in the range of about 2–5 seconds, which is shorter than the 50–100 seconds for the conventional sensors. The stability of the sensor of the present invention is greatly increased greatly. At high temperature, the $Y_2O_3$ can form complex oxides with $SnO_2$ etc., which makes the oxygen absorbed on the surface of $SnO_2$ in the form of $O_2^-$. $O_2^-$ is sensitive to carbon monoxide. Therefore, the sensor of the present invention can detect carbon monoxide at room temperature under low power. Furthermore, the service life of the sensor of the present invention is more than one year. Another advantage of the room temperature carbon monoxide gas sensor of the present invention is that it has no $ThO_2$, and thus no radioactivity pollution will be produced during the preparation and application of the sensor of the present invention.

The present invention will be further described with the following examples.

EXAMPLE 1

2 g $SnO_2$, 0.004 g Pt black, 0.00018 g $La_2O_3$, 0.0005 g $Y_2O_3$, 0.0003 g Cr and 0.0004 g $Al_2O_3$ were weighed into an agate mortar, and then de-ioned water was added to grind the mixture into a paste-like mixture. Two helical coil electrodes having different coil diameters were manufactured with a 0.03 Pt filament, and the prepared paste-like mixture was coated onto the surface of the two electrodes. The smaller coil electrode was inserted into the bigger one to prepare a sensor having a spiral shape. The obtained spiral shape sensor was sintered at 780° C. for 130 minutes in air. After that, the sintered sensor was cooled to room temperature, and aged for 168 hours. The response time of the sensor was less than 10 seconds, the recovery time was less than 10 seconds. In the atmosphere having a carbon monoxide concentration of 25–600 ppm, the response and recovery time of the obtained sensor had linear relationship with I. The properties of the obtained sensor were listed in the Table 1.

EXAMPLE 2

The procedure of Example 1 was repeated with the following raw materials composition: 2 g $SnO_2$, 0.036 g Pt black, 0.1 g $La_2O_3$, 0.04 g $Y_2O_3$, 0.08 g Cr and 0.0004 g $Al_2O_3$. The sintering temperature was 900° C., the sintering time was 80 minutes. The properties of the obtained sensor were listed in the Table 1.

EXAMPLE 3

The procedure of Example 1 was repeated with the following raw materials composition: 2 g $SnO_2$, 0.0065 g Pt black, 0.0008 g $La_2O_3$, 0.0013 g $Y_2O_3$, 0.0009 Cr and 0.0095 g $Al_2O_3$. The sintering temperature was 850° C., the sintering time was 100 minutes. The properties of the obtained sensor were listed in the Table 1.

EXAMPLE 4

The procedure of Example 1 was repeated with the following raw materials composition: 2 g $SnO_2$, 0.0093 g Pt black, 0.0019 g $La_2O_3$, 0.0035 g $Y_2O_3$, 0.0025 g Cr and 0.012 g $Al_2O_3$. The sintering temperature was 800° C., the sintering time was 120 minutes. The properties of the obtained sensor were listed in the Table 1.

EXAMPLE 5

The procedure of Example 1 was repeated with the following raw materials composition: 2 g $SnO_2$, 0.0099 g Pt black, 0.0033 g $La_2O_3$, 0.0056 g $Y_2O_3$, 0.0043 g Cr and 0.034 g $Al_2O_3$. The sintering temperature was 820° C., the sintering time was 110 minutes. The properties of the obtained sensor were listed in the Table 1.

EXAMPLE 6

The procedure of Example 1 was repeated with the following raw materials composition: 2 g $SnO_2$, 0.018 g Pt black, 0.0057 g $La_2O_3$, 0.01 g $Y_2O_3$, 0.085 g Cr and 0.065 g $Al_2O_3$. The sintering temperature was 810° C., the sintering time was 120 minutes. The properties of the obtained sensor were listed in the Table 1.

EXAMPLE 7

The procedure of Example 1 was repeated with the following raw materials composition: 2 g $SnO_2$, 0,025 g Pt black, 0.009 g $La_2O_3$, 0.037 g $Y_2O_3$, 0.029 g Cr and 0.081 g $Al_2O_3$. The sintering temperature was 850° C., the sintering time was 100 minutes. The properties of the obtained sensor were listed in the Table 1.

EXAMPLE 8

The procedure of Example 1 was repeated with the following raw materials composition: 2 g $SnO_2$, 0.031 g Pt black, 0.031 g $La_2O_3$, 0.036 g $Y_2O_3$, 0.013 g Cr and 0.094 g $Al_2O_3$. The sintering temperature was 900° C., the sintering time was 90 minutes. The properties of the obtained sensor were listed in the Table 1.

EXAMPLE 9

The procedure of Example 1 was repeated with the following9 raw materials composition: 2 g $SnO_2$, 0,016 g Pt black, 0.172 g $La_2O_3$, 0.13 g $Y_2O_3$, 0.16 g Cr and 0.14 g $Al_2O_3$. The sintering temperature was 900° C. the sintering time was 100 minutes. The properties of the obtained sensor were listed in the Table 1.

TABLE 1

The relationship between the concentration of CO and $\Delta I$

| Ex. | CO (ppm) $\Delta I$ (mA) | | | | | | |
|---|---|---|---|---|---|---|---|
| | 25 | 50 | 100 | 200 | 300 | 500 | 600 |
| 1 | 1.1 | 2.1 | 4.0 | 8.2 | 12.5 | 20.0 | 23.8 |
| 2 | 1.0 | 2.0 | 3.9 | 8.0 | 11.5 | 19.2 | 24 |
| 3 | 1.2 | 2.1 | 4.3 | 8.4 | 12.7 | 20.5 | 25.4 |
| 4 | 1.4 | 2.3 | 4.5 | 8.9 | 13.5 | 22.1 | 26.6 |
| 5 | 1.3 | 2.2 | 4.2 | 8.1 | 12.5 | 21.0 | 24.9 |
| 6 | 0.9 | 2.0 | 4.0 | 7.8 | 11.9 | 19.7 | 23.9 |
| 7 | 1.1 | 1.9 | 3.9 | 7.7 | 11.7 | 19.5 | 23.1 |
| 8 | 1.5 | 2.7 | 5.2 | 10.1 | 15.6 | 25.8 | 30.0 |
| 9 | 1.2 | 2.2 | 4.3 | 8.1 | 12.0 | 21.6 | 26.1 |

What we claim is:

1. A room temperature carbon monoxide gas sensor comprising two helical coil electrodes made from ϕ0.03–0.05 mm Pt filament, one of which having a greater coil diameter, and the other one having a smaller coil diameter, the length of the coil electrodes being in the range of 0.8–1.4 mm, the one having a greater diameter having a diameter in the range of 0.6–1 mm and being used as an anode, while the smaller diameter one having a diameter between 0.3–0.6 mm and being used as a cathode, the smaller diameter coil electrode being inserted in the greater diameter one, wherein, the two helical coil electrodes are coated by a composition having the following composition:

1 part (weight) of high purity $SnO_2$;
0.002–0.08 (weight) of high purity Pt black;
0.00025–0.065 part (weight) of high purity $Y_2O_3$;
0.00009–0.086 part (weight) of high purity $La_2O_3$;
0.00015–0.08 part (weight) of high purity Cr; and
0.0002–0.07 part (weight) of high purity $Al_2O_3$.

2. A process for preparing a room temperature carbon monoxide gas sensor, comprising the following steps:

(1) preparing two helical coil electrodes with ϕ0.03–0.05 mm Pt filament, one of which having a greater coil diameter, and the other one having a smaller coil diameter, the length of the coil electrode being in the range of 0.8–1.4 mm, the one having a greater diameter having a diameter in the range of 0.6–1 mm and being used as an anode, while the smaller diameter one having a diameter between 0.3–0.6 mm and being used as a cathode;

(2) adding $SnO_2$, $Y_2O_2$, $La_2O_3$, Cr, Pt black and $Al_2O_3$ into an agate mortar to form a mixture at the following proportion,
1 part (weight) of high purity $SnO_2$;
0.002–0.08 (weight) of high purity Pt black;
0.00025–0,065 part (weight) of high purity $YO_3$;
0.00009–0.086 part (weight) of high purity $La_2O_3$;
0.00015–0.08 part (weight) of high purity Cr; and
0.0002–0.07 part (weight) of high purity $Al_2O_3$,
and then adding de-ionized water into the agate mortar to grind the mixture into a paste mixture;

(3) coating the paste mixture obtained in step (2) onto the surfaces of the electrodes obtained in step (1), and then inserting the smaller diameter electrode into the greater diameter electrode to prepare a sensor having spiral shape;

(4) drying the spiral shape sensor obtained in step (3), and then sintering the dried sensor at 780°–900° C. in air for about 80–130 minutes, and cooling and aging the sintered sensor for about 168 hours to obtain a room temperature monoxide gas sensor.

* * * * *